United States Patent
Chasser et al.

(10) Patent No.: US 10,738,216 B2
(45) Date of Patent: Aug. 11, 2020

(54) CARBODIIMIDE CURING FOR PACKAGING COATING COMPOSITIONS

(71) Applicant: PPG Industries Ohio, Inc., Cleveland, OH (US)

(72) Inventors: Anthony M. Chasser, Greensburg, PA (US); Christopher P. Kurtz, Millvale, PA (US); Hongying Zhou, Allison Park, PA (US); William H. Retsch, Jr., Allison Park, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 85 days.

(21) Appl. No.: 16/069,662

(22) PCT Filed: Jan. 13, 2017

(86) PCT No.: PCT/IB2017/050191
§ 371 (c)(1),
(2) Date: Jul. 12, 2018

(87) PCT Pub. No.: WO2017/122171
PCT Pub. Date: Jul. 20, 2017

(65) Prior Publication Data
US 2019/0023940 A1    Jan. 24, 2019

Related U.S. Application Data

(63) Continuation of application No. 15/151,547, filed on May 11, 2016, now abandoned, and a continuation of application No. 14/996,838, filed on Jan. 15, 2016, now abandoned.

(30) Foreign Application Priority Data

Jan. 15, 2016 (EP) .................... 16151619
Jan. 15, 2016 (EP) .................... 16151620
Jan. 15, 2016 (EP) .................... 16151621

(51) Int. Cl.

| | | |
|---|---|---|
| C09D 175/12 | (2006.01) | |
| C09D 5/02 | (2006.01) | |
| C09D 5/03 | (2006.01) | |
| B27N 7/00 | (2006.01) | |
| C08G 18/48 | (2006.01) | |
| C08G 18/66 | (2006.01) | |
| C08G 18/67 | (2006.01) | |
| C08G 18/75 | (2006.01) | |
| C08G 18/79 | (2006.01) | |
| C08G 18/80 | (2006.01) | |
| C08G 18/24 | (2006.01) | |
| C09D 175/16 | (2006.01) | |
| C08G 18/32 | (2006.01) | |
| C08G 18/34 | (2006.01) | |
| C09D 175/02 | (2006.01) | |
| B65D 1/12 | (2006.01) | |
| C07C 275/14 | (2006.01) | |
| C07C 275/26 | (2006.01) | |
| C08G 18/73 | (2006.01) | |
| B27N 3/00 | (2006.01) | |

(52) U.S. Cl.
CPC .......... *C09D 175/12* (2013.01); *B27N 7/005* (2013.01); *B65D 1/12* (2013.01); *C07C 275/14* (2013.01); *C07C 275/26* (2013.01); *C08G 18/246* (2013.01); *C08G 18/3275* (2013.01); *C08G 18/348* (2013.01); *C08G 18/48* (2013.01); *C08G 18/4854* (2013.01); *C08G 18/6692* (2013.01); *C08G 18/672* (2013.01); *C08G 18/73* (2013.01); *C08G 18/751* (2013.01); *C08G 18/755* (2013.01); *C08G 18/792* (2013.01); *C08G 18/8041* (2013.01); *C09D 5/02* (2013.01); *C09D 5/03* (2013.01); *C09D 175/02* (2013.01); *C09D 175/16* (2013.01); *B27N 3/002* (2013.01)

(58) Field of Classification Search
CPC .......... C09D 175/12; C09D 5/02; C09D 5/03; C09D 175/16; C09D 175/02; B27N 7/005; B27N 3/002; C08G 18/4854; C08G 18/6692; C08G 18/672; C08G 18/755; C08G 18/792; C08G 18/8041; C08G 18/246; C08G 18/3275; C08G 18/348; C08G 18/73; C08G 18/751; C08G 18/48; C07C 275/14; C07C 275/26
See application file for complete search history.

(56) References Cited

U.S. PATENT DOCUMENTS

| | | |
|---|---|---|
| 3,294,751 A | 12/1966 | Beitchman |
| 3,420,787 A | 1/1969 | Reymore et al. |
| 3,663,516 A | 5/1972 | Vogt |
| 4,211,683 A | 7/1980 | Wenzel |
| 4,284,572 A | 8/1981 | Stanley et al. |
| 4,990,579 A | 5/1991 | Paar |

(Continued)

FOREIGN PATENT DOCUMENTS

| | | |
|---|---|---|
| CN | 1662618 A | 8/2005 |
| CN | 101098935 A | 1/2008 |

(Continued)

OTHER PUBLICATIONS

Machine English translation of CN101098935.

(Continued)

*Primary Examiner* — Michael C Miggins
(74) *Attorney, Agent, or Firm* — Diane R. Meyers

(57) ABSTRACT

Coated packages and methods for coating such packages is disclosed. The coating compositions comprise a carboxyl-containing polymer and a polycarbodiimide.

23 Claims, No Drawings

(56) References Cited

U.S. PATENT DOCUMENTS

| | | | |
|---|---|---|---|
| 5,030,754 | A | 7/1991 | Speranza et al. |
| 5,047,294 | A | 9/1991 | Schwab et al. |
| 5,574,083 | A | 11/1996 | Brown et al. |
| 5,714,539 | A | 2/1998 | Perez et al. |
| 5,858,549 | A | 1/1999 | Kielbania, Jr. et al. |
| 5,965,466 | A | 10/1999 | Rodrigues et al. |
| 6,051,646 | A | 4/2000 | Nass et al. |
| 6,140,388 | A | 10/2000 | Nass et al. |
| 6,181,311 | B1 | 1/2001 | Hashimoto |
| 6,248,819 | B1 | 6/2001 | Masuda et al. |
| 6,290,867 | B1 | 9/2001 | Kielbania, Jr. et al. |
| 6,875,800 | B2 | 4/2005 | Vanier et al. |
| 6,894,086 | B2 | 5/2005 | Munro et al. |
| 7,033,526 | B2 | 4/2006 | Figiel et al. |
| 7,605,194 | B2 | 10/2009 | Ferencz et al. |
| 8,153,344 | B2 | 4/2012 | Faler et al. |
| 8,846,156 | B2 | 9/2014 | Swarup et al. |
| 2004/0266921 | A1 | 12/2004 | Rodrigues et al. |
| 2005/0113269 | A1 | 5/2005 | Landa et al. |
| 2005/0171300 | A1 | 8/2005 | Moens et al. |
| 2008/0004361 | A1 | 1/2008 | Palermo |
| 2009/0197202 | A1 | 8/2009 | Matsumura |
| 2009/0246343 | A1 | 10/2009 | Wu et al. |
| 2011/0070372 | A1 | 3/2011 | Faucher et al. |
| 2011/0070374 | A1 | 3/2011 | Ambrose et al. |
| 2011/0151128 | A1 | 6/2011 | Boggs et al. |
| 2011/0244157 | A1 | 10/2011 | Singer et al. |
| 2014/0011018 | A1 | 1/2014 | Diehl et al. |
| 2014/0023782 | A1 | 1/2014 | Kunz et al. |
| 2014/0030535 | A1 | 1/2014 | Makotky et al. |
| 2014/0319133 | A1 | 10/2014 | Castlebert et al. |
| 2015/0225339 | A1 | 8/2015 | Niedermair et al. |
| 2015/0344732 | A1 | 12/2015 | Witt-Sanson et al. |
| 2016/0280951 | A1 | 9/2016 | Drumright et al. |

FOREIGN PATENT DOCUMENTS

| | | |
|---|---|---|
| CN | 102296290 A | 12/2011 |
| CN | 103145588 A | 6/2013 |
| CN | 103502354 A | 1/2014 |
| CN | 104955911 A | 9/2015 |
| EP | 0519186 A1 | 12/1992 |
| EP | 0866082 A1 | 9/1998 |
| EP | 1541640 A1 | 6/2005 |
| EP | 1525274 B1 | 3/2007 |
| EP | 1935878 A1 | 6/2008 |
| EP | 2316868 A1 | 5/2011 |
| EP | 2447059 A2 | 5/2012 |
| EP | 2746353 A1 | 6/2014 |
| EP | 2773710 B1 | 4/2016 |
| JP | H111335594 A | 12/1999 |
| JP | 2001192609 A | 7/2001 |
| JP | 5146327 B2 | 2/2013 |
| JP | 2014148618 A | 8/2014 |
| RU | 2376284 C1 | 10/2009 |
| RU | 2009103017 A | 8/2010 |
| WO | 2004000958 A1 | 12/2003 |
| WO | 2006132910 A1 | 12/2006 |
| WO | 2008076669 A1 | 6/2008 |
| WO | 2009095471 A1 | 8/2009 |
| WO | 2011019840 A1 | 2/2011 |
| WO | 2012118500 A1 | 9/2012 |
| WO | 2012118501 A1 | 9/2012 |
| WO | 2012162301 A1 | 11/2012 |
| WO | 2013191825 A1 | 12/2013 |
| WO | 2014025411 A1 | 2/2014 |
| WO | 2015077687 A1 | 5/2015 |

OTHER PUBLICATIONS

Machine English translation of CN103145588.
Machine English translation of EP0519186.
Machine English translation of the Abstract only of JP2001192609.
Machine English translation of JPH11335594.
Machine English translation of RU2376284.
Machine English translation of RU2009103017.
The International Search Report and the Written Opinion of the International Searching Authority for International Application No. PCT/IB17/50191.

CARBODIIMIDE CURING FOR PACKAGING COATING COMPOSITIONS

FIELD OF THE INVENTION

The present invention relates to coated packages and to methods of applying a coating to the packages in which the coating composition is based on resinous binders containing polycarbodiimide curing agent.

BACKGROUND OF THE INVENTION

A wide variety of coatings have been used to coat the surfaces of packages such as food and beverage containers. For example, metal cans are sometimes coated using coil coating or sheet coating operations, that is, a coil or sheet of steel or aluminum is coated with a suitable composition and cured. The coated substrate is then formed into the can body or can end. Alternatively, the coating composition may be applied, for example, by spraying and dipping, to the formed can and then cured. Coatings for food and beverage containers should preferably be capable of high speed application to the substrate and provide the necessary properties when cured to perform in a demanding end use environment. For example, the coating should be safe for food contact and have excellent adhesion to the substrate.

To achieve the necessary coating properties, the coatings are thermosetting in nature, that is, the coating composition is based on a resinous binder that contains a polymeric material that contains active hydrogens, for example, a (meth)acrylic polymer or a polyester, each of which contain hydroxyl groups, and a curing agent that is reactive with the active hydrogens to form a crosslinked or thermoset coating. The curing agent of choice is a phenol-formaldehyde or an amine such as melamine, benzoguanamine or urea-formaldehyde condensate. Unfortunately, such curing agents release formaldehyde during the curing or crosslinking reaction.

This formaldehyde can be a strong irritant when allowed to accumulate in an enclosed space such as, for example, a curing oven. It is also suspected of being hazardous to the health of humans when allowed to accumulate to abnormally high levels in the ambient atmosphere. It is, therefore, desirable to eliminate formaldehyde emissions during the curing operation. One way to do this is to use an alternative curing agent that does not release formaldehyde yet provides the necessary properties for coating food or beverage containers such as adhesion, flexibility and resistance to acidic foods or beverages such as tomatoes and isotonic beverages.

SUMMARY OF THE INVENTION

The present invention provides a coated package comprising a coating applied to the surface of the package, the coating being derived from a composition comprising:
(a) a carboxyl-containing polymer, and
(b) a polycarbodiimide having the following structural units (a) or (b) including mixtures thereof:

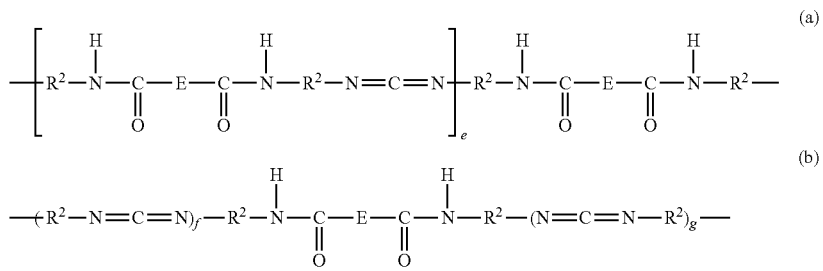

where e is an integer of from 2 to 20; f and g are each at least 1, and f+g is an integer up to 20; E is a radical selected from

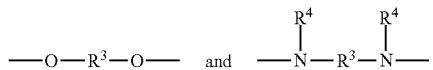

where $R^2$ comprises a cyclic radical and $R^3$ is a linear hydrocarbon radical containing at least 4 carbon atoms and $R^4$ is hydrogen or an alkyl radical.

The invention also provides a method of applying a crosslinked coating to a package comprising:
(a) providing a coating composition comprising:
(i) a carboxyl-containing polymer, and
(ii) a polycarbodiimide having the following structural units (a) or (b) including mixtures thereof:

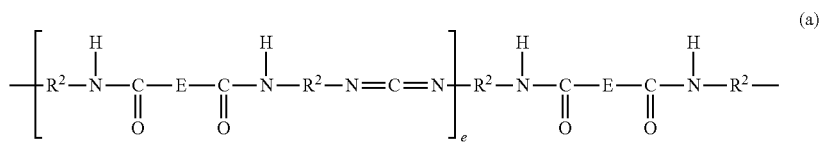

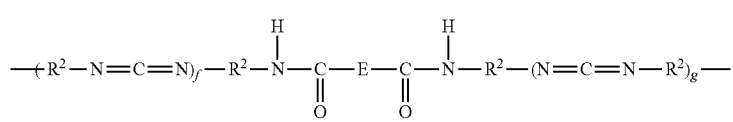

(b)

where e is an integer of from 2 to 20; f and g are each at least 1, and f+g is an integer up to 20; E is a radical selected from

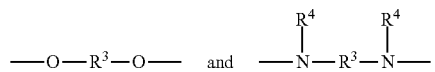

where $R^2$ comprises a cyclic radical and $R^3$ is a linear hydrocarbon radical containing at least 4 carbon atoms and $R^4$ is hydrogen or an alkyl radical;

(b) applying the coating composition to a substrate prior to or after forming the substrate into a package or a portion thereof; and (c) heating the coated substrate to a temperature and for a time sufficient to crosslink the coating composition.

DETAILED DESCRIPTION

As used herein, the term "hydrocarbon group or radical" means a group or radical containing carbon and hydrogen (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). The term "aliphatic group" means a saturated or unsaturated linear or branched hydrocarbon group. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "cyclic group" or "cyclic radical" means a closed ring hydrocarbon group or radical that may be alicyclic group or aromatic group, both of which can include heteroatoms. The term "alicyclic group" means a cyclic hydrocarbon group having properties resembling those of aliphatic groups such as cycloaliphatic and alkaryl. Group and radical are used interchangeably.

A group that may be the same or different is referred to as being "independently" something.

The term "crosslinker" or "curing agent" refers to a molecule capable of forming a covalent linkage between polymers or between two different regions of the same polymer.

The term "dispersed in aqueous medium" means that a polymer and crosslinker can be mixed into aqueous medium to form a stable mixture, that is, the mixture does not separate into immiscible layers within an hour after mixing.

The term "aqueous medium" means water or a mixture of water and organic solvent.

The term "food-contacting surface" refers to the surface of a container such as an inner surface of a food or beverage container that is in contact with, or intended for contact with, a food or beverage product. By way of example, an interior surface of a metal substrate of a food or beverage container, or a portion thereof such as a can end or a can body, is a food-contacting surface even if the interior metal surface is coated with a coating composition.

The term "package" means anything used to contain another item, particularly for shipping from a point of manufacture to a consumer, and for subsequent storage by a consumer. A package will be therefore understood as something that is sealed so as to keep its contents free from deterioration until opened by a consumer. The manufacturer will often identify the length of time during which the food or beverage will be free from spoilage, which typically ranges from several months to years. Thus, the packages of the present invention are distinguished from open containers or bakeware in which a consumer might make and/or store food since it is not sealed; such a container would only maintain the freshness or integrity of the food item for a relatively short period. A package according to the present invention can be made of metal or non-metal, for example, plastic or laminate, and be in any form. An example of a suitable package is a laminate tube. Another example of a suitable package is a food or beverage container, typically in the form of a metal can. The term "metal can" includes any type of metal can, container or any type of receptacle or portion thereof that is sealed by the food/beverage manufacturer to minimize or eliminate spoilage of the contents until such package is opened by the consumer. Example of a metal can is a food can; the term "food can(s)" is used herein to refer to cans, containers or any type of receptacle or portion thereof used to hold any type of food and/or beverage. The term "metal can(s)" specifically includes food cans and also specifically includes "can ends" including "E-Z open ends", which are typically stamped from can end stock and used in conjunction with the packaging of food and beverages. The term "metal cans" also specifically includes metal caps and/or closures such as bottle caps, screw top caps and lids of any size, lug caps, and the like. The metal cans can be used to hold other items as well, including, but not limited to, personal care products, bug spray, spray paint, and any other compound suitable for packaging in an aerosol can. The cans can include "two piece cans" and "three-piece cans" as well as drawn and ironed one-piece cans; such one piece cans often find application with aerosol products. Packages coated according to the present invention can also include plastic bottles, plastic tubes, laminates and flexible packaging, such as those made from PE, PP, PET and the like. Such packaging could hold, for example, food, toothpaste, personal care products and the like.

The term "colorant" means any substance that imparts color and/or other opacity and/or other visual effect to the composition.

The term "on", when used in the context of a coating applied on a surface or substrate, includes both coatings applied directly or indirectly to the surface or substrate. Thus, for example, a coating applied to a primer layer overlying a substrate constitutes a coating applied on the substrate.

Unless otherwise indicated, the term "polymer" includes both homopolymers and copolymers (e.g., polymers of two or more different monomers) and oligomers. Resin is used simultaneously with polymer.

Acrylic and methacrylic monomers and polymers are designated as (meth)acrylic monomers and polymers.

Molecular weights are on a number average or weight average basis as indicated and are determined by gel permeation chromatography using polystyrene standards.

As used herein, "a", "an", "the", "at least one" and "one or more" are used interchangeably. Thus, for example, a coating composition that comprises "a" polyether can be interpreted to mean that the coating composition includes "one or more" polyethers.

Also herein, the recitations of numerical ranges by endpoints include all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 4 to 5, etc.).

The polycarbodiimides of the present invention are prepared by reacting an organic group containing a polyisocyanate in the presence of a suitable catalyst to form a polycarbodiimide having terminal NCO-functionality, wherein an active hydrogen-containing compound is added before, during or after polycarbodiimide formation.

The polyisocyanate that is used in the instant invention can be an aliphatic, including cycloaliphatic, or an aromatic polyisocyanate or mixture of the two. Aliphatic including cycloaliphatic polyisocyanates and alkaryl polyisocyanates are particularly suitable. The polyisocyanates can contain from 2 to 4, such as 2 isocyanate groups per molecule. Examples of suitable higher polyisocyanates are 1,2,4-benzene triisocyanate and polymethylene polyphenyl isocyanate. Examples of suitable aromatic diisocyanates are 4,4'-diphenylmethane diisocyanate, 1,3-phenylene diisocyanate, 1,4-phenylene diisocyanate and tolylene diisocyanate. Examples of suitable aliphatic diisocyanates are straight chain aliphatic diisocyanates such as 1,4-tetramethylene diisocyanate and 1,6-hexamethylene diisocyanate and alkaryl polyisocyanates such as m-tetramethylxylene diisocyanate. Also, cycloaliphatic diisocyanates can be employed. Examples include 1,4-cyclohexyl diisocyanate, isophorone diisocyanate, alpha, alpha-xylylene diisocyanate and 4,4-methylene-bis(cyclohexyl isocyanate). Substituted organic group-containing polyisocyanates can also be used in which the substituents are nitro, chloro, alkoxy and other groups that are not reactive with hydroxyl groups or active hydrogens and provided the substituents are not positioned to render the isocyanate group unreactive.

The active hydrogen-containing compound used in the preparation of the polycarbodiimide is a chain extender or spacer linking polyisocyanates together to form NCO-adducts or to link NCO-functional polycarbodiimides together. Any suitable organic compound containing active hydrogens may be used. The term "active hydrogen atoms" refers to hydrogens which, because of their position in the molecule, display activity according to the Zerewitinoff test. Accordingly, active hydrogens include hydrogen atoms attached to oxygen or nitrogen, and thus useful compounds will include those having at least two of these groups (in any combination)

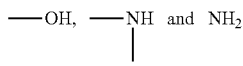

The moieties attached to each group can be aliphatic, including cycloaliphatic, aromatic, or of a mixed type with aliphatic being particularly suitable.

The active hydrogen-containing material can contain from 2 to 4, particularly suitable 2 active hydrogens per molecule.

Examples of such compounds include amines, which includes polyamines, aminoalcohols, mercapto-terminated derivatives, and alcohols that includes polyhydroxy materials (polyols) that are particularly suitable because of the ease of reaction with polyisocyanates. Also polyols generally give no side reactions, giving higher yields of urethane product with no by-product and the products are hydrolytically stable. Also, with regard to polyols, there are a wide variety of materials available which can be selected to give a wide spectrum of desired properties. In addition, the polyols have desirable reaction rates with polyisocyanates. Both saturated and unsaturated active hydrogen-containing compounds can be used, but saturated materials are particularly suitable because of superior coating properties.

The polyhydroxyl materials or polyols can be either low or high molecular weight materials and in general will have average hydroxyl values as determined by ASTM designation E-222-67, Method B, of 2000 and below, such as between 2000 and 10. The term "polyol" is meant to include materials having an average of two or more hydroxyl groups per molecule.

The polyols include low molecular weight diols, triols and higher molecular weight polyols, low molecular weight amide-containing polyols and higher polymeric polyols such as polyester polyols, polyether polyols, polycarbonate polyols and hydroxy-containing (meth)acrylic polymers. The polymers typically have hydroxyl values of from 10 to 180. Also, the polymers typically have number average molecular weights of 96 to 10,000.

The low molecular weight diols, triols and higher alcohols useful in the instant invention are known in the art. They have hydroxy values of 200 or above, usually within the range of 200 to 2000. Such materials include aliphatic polyols, particularly alkylene polyols containing from 4 to 18 carbon atoms. Examples include 1,4-butanediol and 1,6-hexanediol. Also useful are polyols containing ether linkages such as diethylene glycol and tetraethylene glycol.

To form the polycarbodiimide, the polyisocyanate with or without the active hydrogen-containing compound is condensed with the elimination of carbon dioxide to form the polycarbodiimide, that is, a polymer containing $-\!\!\left\{\mathrm{N}\!\!=\!\!\mathrm{C}\!\!=\!\!\mathrm{N}\right\}_n\!\!-$ units where n=2 to 20, such as 2 to 10.

The condensation reaction is typically conducted by taking the solution of the polyisocyanate and heating in the presence of suitable catalyst. Examples of catalyst include 1-ethyl-3-phospholine, 1-ethyl-3-methyl-3-phospholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the polyisocyanate being used. A concentration range of 0.05-5 parts of catalyst per 100 parts of adduct is generally suitable.

The resulting polycarbodiimide has terminal NCO groups that can then be reacted with an active hydrogen-containing hydrophilic compound to impart hydrophilicity to the polycarbodiimide enabling it to be dispersed in water. The hydrophilic compounds are typically compounds that are miscible with water in amounts of at least 40% by weight, such as at least 45% by weight, (% by weight based on total weight of hydrophilic compound and water) and in certain instance are miscible with water in all proportions. Miscible means the hydrophilic compound will not form a separate phase. The method used for determining water solubility is the shake flask method OPPTS 830.7840 as published by the Environmental Protection Agency (EPA).

The hydrophilic compound is a polyether alcohol or polyether amine or mixtures thereof having a polyether backbone, typically based on ethylene oxide or mixed ethylene oxide and propylene and having a molecular weight greater than 500, such as at least 1000 on a number average basis. Typical alcohols and amines have the following structural formula:

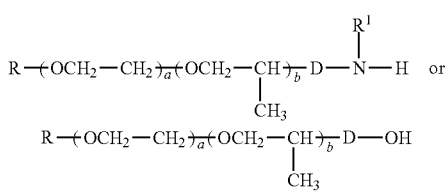

where R is $C_1$ to $C_4$ alkyl; a is 5 to 50 and b is 0 to 35, and when b is present the mole ratio of a to b is at least 1:1; $R^1$ is hydrogen or a hydrocarbon radical and D is a divalent linking group or a chemical bond.

Reaction of the polyether alcohol or amine with the NCO-containing carbodiimide is conducted with a stoichiometric equivalent of amine to NCO equivalents or a slight excess of alcohol or amine and at a temperature typically from 80 to 110° C. until an IR spectrum of the reaction mixture indicates substantially no remaining NCO functionality.

Depending on when the active hydrogen chain extender or spacer is used in the reaction, the polycarbodiimide has a structure such that each carbodiimide unit or polycarbodiimide unit is attached to a unit selected from urethane, thiourethane urea, thiourea and a hydrophilic unit occurs at one or terminal positions of the polycarbodiimide via a urethane or urea linkage.

Typically, the polycarbodiimide has a weight average molecular weight of 2600 to 12,000, such as 3000 to 10,000, and a diimide equivalent weight (number average molecular weight/number of carbodiimide groups) of at least 600, such as 600 to 2000.

When the active hydrogen chain extender is added before or during polycarbodiimide formation, that is, is used to chain extend a polyisocyanate to form an NCO-adduct, the polycarbodiimide can be represented from the following structural formula when the polyisocyanate and the active hydrogen-containing compound are difunctional:

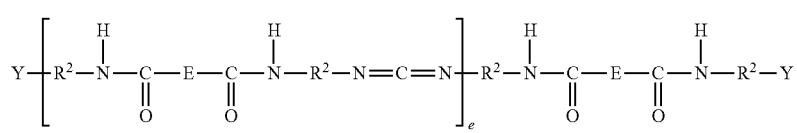

where e with reference to (I) is an integer of from 2 to 20, such as 2 to 10; E with reference to (I) is a radical selected from

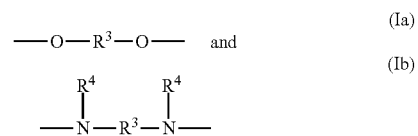

where $R^2$ with reference to (I) is a cyclic radical such as a cycloaliphatic or an alkaryl radical that may contain 6 to 20 carbon atoms such as those of the structure:

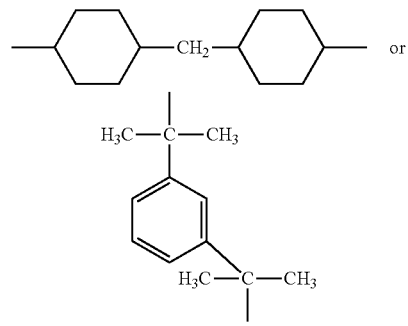

$R^3$ with reference to (Ia) and (Ib) is a linear hydrocarbon radical optionally including hetero atoms containing at least 4 carbon atoms such as a polyethylene group having a number average molecular weight of 96 to 10,000. $R^4$ with reference to (Ib) is hydrogen or a hydrocarbon radical such as alkyl containing from 1 to 4 carbon atoms. Y is a radical of the structure:

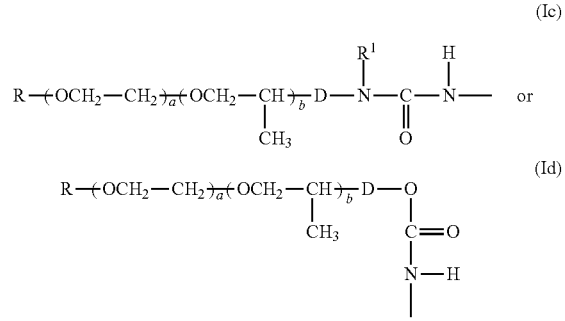

where R with reference to (Ic) and (Id) is $C_1$ to $C_4$ alkyl; a with reference to (Ic) and (Id) is 5 to 50 and b with reference to (Ic) and (Id) is 0 to 35, and when b with reference to (Ic) and (Id) is present the mole ratio of a to b with reference to (Ic) and (Id) is at least 1:1; $R^1$ with reference to (Ic) and (Id) is hydrogen or a hydrocarbon radical and D with reference to (Ic) and (Id) is a divalent linking group or a chemical bond.

When the active hydrogen chain extender is added after polycarbodiimide formation, that is, is used to chain extend an NCO-functional polycarbodiimide, the polycarbodiimide can be represented from the following structural formula when the NCO-functional polycarbodiimide and the active hydrogen-containing compound are difunctional.

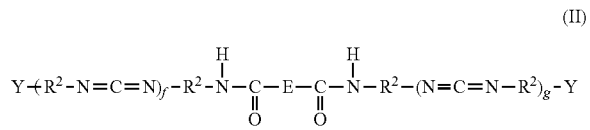

(II)

where f and g each with reference to (II) are each at least 1, and f+g with reference to (II) is an integer up to 20 such as up to 10; E with reference to (II) is a radical selected from

 and (IIa)

 (IIb)

where $R^2$, $R^3$, $R^4$ and Y with reference to (II), (IIa) and (IIb) have the meanings mentioned above for (I).

Organic solvent can optionally be present in the synthesis of the polycarbodiimide. Polar water miscible solvents such as N-methyl pyrrolidone can be used in amounts of about 5-25 percent by weight based on weight of the reaction mixture.

The polycarbodiimide prepared as described above is dispersed in aqueous medium by adding the polycarbodiimide to the aqueous medium or adding the aqueous medium to the polycarbodiimide. Addition is done slowly with mild agitation. Typically, the carboxyl-containing polymer is present in the aqueous medium during the dispersion step.

The polycarbodiimide as described above is used as a crosslinker for thermosetting water-based coating compositions in combination with a carboxyl group-containing polymer.

The carboxyl-containing polymer may be, for example, a carboxyl-containing polyester polymer or a (meth)acrylic polymer.

The carboxyl-containing polyester polymer can be prepared by condensation in the conventional manner.

The carboxyl-containing polyester polymer is produced from a polyol component and a polyacid component.

Examples of polyols are those having two or more hydroxy groups within each molecule, such as triols such as trimethylolpropane and hexanetriol, and diols such as propylene glycol, neopentyl glycol, butylene glycol, hexylene glycol, octylene glycol, 1,6-hexanediol, 1,8-octanediol, 1,9-nonanediol, 1,10-decanediol, 1,12-dodecanediol, 1,2-cyclohexanediol, 1,3-cyclohexanediol, 1,4-cyclohexanediol, hydrogenated bisphenol A, caprolactone diol and bishydroxyethyltaurine.

Examples of polyacids are those having two or more carboxyl groups within each molecule, for example aromatic dicarboxylic acids such as phthalic acid and isophthalic acid, aliphatic dicarboxylic acids such as adipic acid, azelaic acid and tetrahydrophthalic acid, and tricarboxylic acids such as trimellitic acid. The carboxyl-functional polyesters typically have acid values of at least 2, such as 5 to 100 and hydroxyl values less than 200, such as 20 to 150.

The carboxyl-containing (meth)acrylic polymer can be obtained in the conventional manner, specifically by solution or emulsion polymerization.

For example, the carboxyl-containing (meth)acrylic polymer can be obtained from a carboxyl-containing ethylenically unsaturated monomer and another ethylenically unsaturated monomer.

The carboxyl-containing ethylenically unsaturated monomer specifically includes acrylic acid, methacrylic acid, ethacrylic acid, crotonic acid, maleic acid, fumaric acid, itaconic acid, half esters thereof such as maleic acid ethyl ester, fumaric acid ethyl ester and itaconic acid ethyl ester, succinic acid mono (meth)acryloyloxyethyl ester, phthalic acid mono (meth)acryloyloxyethyl ester and the like. The carboxyl-containing ethylenically unsaturated monomer may comprise two or more species.

The other ethylenically unsaturated monomer specifically includes hydroxy-containing ethylenically unsaturated monomers such as 2-hydroxyethyl acrylate, 2-hydroxyethyl methacrylate, 4-hydroxybutyl acrylate, and 4-hydroxybutyl methacrylate. Nonfunctional ethylenically unsaturated monomers such as styrene, alpha-methylstyrene, acrylate esters (e.g. methyl acrylate, ethyl acrylate, butyl acrylate, 2-ethylhexyl acrylate) and methacrylate esters (e.g. methyl methacrylate, ethyl methacrylate, butylmethacrylate, isobutylmethacrylate, tert-butyl methacrylate, 2-ethylhexyl methacrylate, lauryl methacrylate) are typically present. The above other ethylenically unsaturated monomer may comprise two or more species. The carboxyl-containing (meth) acrylic polymers typically have acid values of at least 2, such as 5 to 100.

The calculated molar ratio of carbodiimide to carboxylic acid is 0.05 to 5/1, such as 0.05 to 2/1.

The coating compositions used in the invention are in the form of an aqueous dispersion in which the resinous phase is dispersed in aqueous medium. The aqueous medium of the dispersion may consist entirely of water in some cases but, more commonly, will consist of a mixture of water and water-soluble or water-miscible organic solvents. Suitable organic solvents are the ether type alcohols, such as ethylene glycol monobutyl ether (butyl Cellosolve), ethylene glycol monoethyl ether (ethyl Cellosolve) and the like, and lower alkanols having 2 to 4 carbon atoms such as ethanol, propanol, isopropanol, butanol, and the like. Minor proportions of hydrocarbon solvents such as xylene, toluene, and the like may also be present in the aqueous medium. The aqueous medium may contain from about 60 percent to about 100 percent by weight of water and from about 0 percent to about 40 percent by weight of organic solvent. The percentage by weight is based on total weight of the aqueous medium.

To disperse the resinous phase in the aqueous medium, the carboxyl-containing polymer is at least partially neutralized with a base such as an amine. Examples of amines include ammonia, monoethanolamine and diethanolamine. Typically, the amine will neutralize at least 25 percent, such as at least 50 percent of the acid equivalents in the carboxyl-containing polymer.

The polycarbodiimide can then be combined with the (meth)acrylic polymer salt and the mixture dispersed in the aqueous medium. The resin solids content of the aqueous dispersion is typically from 30 to 50, such as 38 to 42 percent by weight based on total weight of the aqueous dispersion.

The coating compositions used in the present invention may also include optional ingredients that do not adversely affect the coating composition or a cured coating composition resulting therefrom. Such optional ingredients are typically included in a coating composition to enhance composition aesthetics to facilitate manufacturing, processing, handling and application of the composition, and to further improve the particular functional property of a coating composition or a cured coating composition resulting therefrom.

Such optional ingredients include, for example, catalysts, colorants, fillers, lubricants, anticorrosive agents, flow agents, thixotropic agents, dispersing agents, antioxidants, adhesion promoters, and mixtures thereof. Each optional ingredient is included in a sufficient amount to serve its intended purpose, but not in such amount to adversely affect the coating composition or a cured coating composition resulting therefrom.

In certain embodiments, such as when the coating compositions are used on the interior or food-contacting surface of a food or beverage container, the compositions and/or the resultant coatings on the container may be substantially free, may be essentially free and/or may be completely free of bisphenol A and derivatives or residues thereof, including bisphenol A ("BPA") and bisphenol A diglycidyl ether ("BADGE"). Such compositions and/or coatings are sometimes referred to as "BPA non intent" because BPA, including derivatives or residues thereof, are not intentionally added but may be present in trace amounts because of impurities or unavoidable contamination from the environment. The compositions and/or coatings can also be substantially free and may be essentially free and/or may be completely free of bisphenol F and derivatives or residues thereof, including bisphenol F and bisphenol F diglycidyl ether ("BFDGE"). The term "substantially free" as used in this context means the compositions and/or coatings contain less than 1000 parts per million (ppm), "essentially free" means less than 100 ppm and "completely free" means less than 20 parts per billion (ppb) of any of the above-mentioned compounds, derivatives or residues thereof.

The coating compositions are particularly well adapted for use as internal or external surface coatings for food or beverage containers, i.e., two-piece cans and three-piece cans. The compositions are typically applied to metal substrates and cured into films at high speed, on high-speed coating lines (e.g., coil coating lines). The coating agents are typically applied in a roller coating process either continuously on coil lines or batch-wise on sheet coating lines to thin metals such as aluminum, tinplate, tin-free steel or chromed steel, and then reacted at high temperatures. The coated metals thus produced are then shaped to form the desired metal packaging articles by processes such as, for example, deep-drawing, stamping, creasing, welding and flanging. This processing requires very high flexibility and excellent adhesion of the coating agents used. In such applications, the coatings preferably should not experience any change in the protective function due to the forming processes and, in addition, should preferably exhibit suitable adhesion with no breaks in the coating.

The compositions are generally applied to metal sheets in one of two ways. The coated metal sheets may be fabricated into can bodies or ends in a later stage of the manufacturing operation.

One process, called the sheet bake process, involves roll coating large planar metal sheets. These sheets are then placed upright in racks and the racks are typically placed in ovens for about 10 minutes to achieve peak metal temperatures of about 180° C. to about 205° C. In a second process known as coil coating, large rolls of thin gage metal (e.g., steel or aluminum) are unwound, roll coated, heat cured and rewound. During the coil coating process, the total residence time in the curing ovens will vary from about 2 seconds to about 20 seconds with peak metal temperatures typically reaching about 215° C. to about 300° C.

A coil coating is described as the coating of a continuous coil composed of a metal (e.g., steel or aluminum). Once coated, the coating coil is typically subjected to a short thermal curing cycle, which leads to the drying and curing of the coating. Coil coatings provide coated metal (e.g., steel and/or aluminum) substrates that can be fabricated into formed articles such as two-piece food cans, three-piece food cans, food can ends, beverage can ends and the like.

A sheet coating is described as the coating of separate pieces of a variety of materials (e.g., steel or aluminum) that have been pre-cut into square or rectangular planar "sheets". Typical dimensions of these sheets are approximately one square meter. Once coated, each sheet is cured. Once dried and cured, the sheets of the coated substrate are collected and prepared for subsequent fabrication. Sheet coatings provide coated metal (e.g., steel or aluminum) substrate that can be successfully fabricated into formed articles such as two-piece food cans, three-piece food cans, food can ends, drawn and ironed cans, beverage can ends and the like. For three-piece cans, the coated planar sheet is slit into body blanks and then formed into cylinders and welded at the side seam. A can end is affixed to an open end of the container, the cylinder filled with food or beverage and a can end affixed to the open end of the container and the container sealed.

EXAMPLES

The following examples are offered to aid in understanding of the present invention and are not to be construed as limiting the scope thereof. Unless otherwise indicated, all parts and percentages are by weight.

Polycarbodiimides of the present invention were mixed with different acrylic latex polymers on either a wt % basis or acid/carbodiimide equivalent ratio.

Carboxyl containing polymer "A" is a partially amine-neutralized carboxylic acid group-containing (meth)acrylic latex polymer that has a solid content of 40.0% when measured after heating a sample to 110° C. for 1 hour, a measured acid value of 5.2 mg KOH/g, and a theoretical hydroxyl content of 50.8 mg KOH/g.

Carboxyl containing polymer "B" is a partially amine-neutralized carboxylic acid group-containing (meth)acrylic latex polymer that has a solid content of 40.0% when measured after heating a sample to 110° C. for 1 hour, a measured acid value of 10.2 mg KOH/g, and a theoretical hydroxyl content of 50.8 mg KOH/g.

These (meth)acrylic latex polymers are prepared generally according to the procedures outlined by Perez in U.S. Pat. No. 5,714,539.

Example C

A polycarbodiimide was prepared from the following charges:

| Ingredients | Parts by Weight |
|---|---|
| Charge #1 | |
| Desmodur W[1] | 262.3 |
| Phospholene oxide[2] | 2 |

-continued

| Ingredients | Parts by Weight |
|---|---|
| Charge #2 | |
| Dibutyltin dilaurate | 0.02 |
| Charge #3 | |
| Tetraethylene glycol[3] | 26.3 |
| Carbowax[4] | 63.2 |
| Charge #4 | |
| Jeffamine M1000 (XTJ-506)[5] | 94.7 |
| Charge #5 | |
| Deionized water | 650 |
| Abex 2005[6] | 20.8 |

[1]Desmodur W is methylene-bis-(4-cyclohexyl diisocyanate) from Bayer Material Science, LLC.
[2]Phospholene oxide is 1-methyl-1-oxo-phospholene from Clariant Chemical.
[3]Tetraethylene glycol is purchased from Dow Chemical Co.
[4]Carbowax is methoxy polyethylene glycol, 350 MW from Dow Chemical Co.
[5]Jeffamine M1000 (XTJ-506) is a polyether monoamine from Huntsman (mole ratio of EO/PO = 6.3, MW = 1000).
[6]Abex 2005 is a proprietary anionic surfactant from Rhodia.

Charge #1 was added to a 2-liter, 4-necked flask equipped with a motor driven stainless steel stir blade, a water-cooled condenser, a nitrogen sparge, and a heating mantle with a thermometer connected through a temperature feedback control device. The contents of the flask were heated to 160° C. and held at that temperature until the isocyanate equivalent weight (NCO EQ Wt) measured >410 eq/g by titration ( ). The temperature was then decreased to 90° C. and NCO EQ Wt was measured again (426.7). At 90° C., charge #2 was added first and followed by adding charge #3 over 20 minutes. The reaction mixture was held at 90-100° C. until the NCO equivalent weight stalled at about 3619. Charge #4 was added over 10 minutes at 90-100° C. The mixture was held at 90-100° C. until IR spectroscopy showed the absence of the characteristic NCO band. Charge #5 was preheated to 80° C. and added into the flask over 20 minutes while maintaining the temperature below 80° C. The reaction product was cooled to room temperature.

The acrylic latex polymer was placed into an appropriately sized container. To the container was added enough deionized water to bring the final solids of the formulated polymer to 37%. The mixture was agitated using an overhead air supplied stirrer attached with a paddle blade. While the mixture was under agitation, 10% on solids of ethylene glycol mono-2-ethylhexyl ether (purchased from Eastman as Ektasolve EEH) was added and allowed to incorporate. After the addition of the Ektasolve EEH, the polycarbodiimide crosslinker was added and held under agitation until the resulting mixture became homogenous.

Various crosslinkers were used to evaluate the effectiveness of the present invention. The crosslinkers included a melamine-formaldehyde condensate Resimene HM 2608 (purchased from Ineos Melamines, LLC), a hydroxyalkyl amide Primid XL-552 (purchased from EMS-Griltech), a comparative polycarbodiimide Carbodilite V-04 (purchased from GSI Exim America, Inc.) and the polycarbodiimide of Example C.

The polycarbodiimide Carbodilite V-04 had a carbodiimide equivalent of 335 and did not contain a chain extender or spacer.

The resulting mixtures were drawn down on 0.0082" aluminum substrate to a wet film thickness of 25 microns. The film was baked for 10 seconds in a 290° C. conveyor oven. The substrate reached a Peak Metal Temperature of 450° F. (232° C.).

Testing Methods

After baking, the resulting coatings were checked for MEK solvent resistance by determining the number of double rubs by hand it took to soften and break through the coating with a rag saturated with methyl ethyl ketone. This test is a measure of the degree of cure. High degrees of cure are necessary in coatings for metal food and beverage containers to prevent corrosion of the underlying metal.

The final coatings were also evaluated using the Acetic Acid Test. The "Acetic Acid" test is designed to measure the resistance of a coating to a boiling 3% acetic acid solution. This test simulates the resistance of the coating to acid-containing foods such as tomatoes and beverages such as isotonic drinks. The solution is prepared by mixing 90 grams of glacial acetic acid (product of Fisher Scientific) into 3000 grams of deionized water. Coated strips are partially immersed into the boiling acetic acid solution for 30 minutes. The strips are then rinsed and cooled in deionized water, dried, and immediately rated for blister, blush and adhesion as described below.

Blister resistance is a Pass/Fail test. Each panel was visually inspected for the presence of blistering. Blistering is evidenced by the formation of bubbles in the coating during the Acetic Acid test. A Pass rating is given if there is no detectable blistering of the coating.

Blush resistance measures the ability of a coating to resist attack by various testing solutions. When the coated film absorbs test solution, it generally becomes cloudy or looks white. Blush is measured visually using a scale of 1-10 where a rating of "10" indicates no blush and a rating of "0" indicates complete whitening of the film. Blush ratings of at least 6 are typically desired for commercially viable coatings. The coated panel tested is 2×4 inches (5×10 cm) and the testing solution covers half of the panel being tested so you can compare blush of the exposed panel to the unexposed portion.

Immediately after measuring the blush resistance, the adhesion of the coated panels were checked using ASTM D3359 Method B "Standard Test Methods for Measuring Adhesion by Tape Test". The adhesive tape used is Scotch Packaging Tape 610. The crosshatch pattern of cuts is made over the liquid/air interface on the coated panel. The results are recorded as Pass/Fail. Any amount of coating removal by the adhesive tape is considered as a Fail.

Coating flexibility was measured by the Wedge Bend test using a BYK-Gardner "Coverall" Bend and Impact Tester. Coating flexibility is necessary for the coating to withstand the container fabrication process, for the drawing operation in the fabrication of a 2-piece can and the stamping process for can ends. In the Wedge Bend test, a 2×4 inch (5×10 cm) coated test panel is first bent double over the ⅛" rod so that the coated surface is on the outside. The bent panel is placed between the parts of the hinge. The impact tool, flat face down, is dropped from a height needed to deliver 40 inch-pounds of impact force onto the upper part of the hinge. The impacted test panel will have a wedge shape where one end of the coated metal impinged upon itself and a ⅛ inch space remained on the opposite end.

After completing the wedge bend, the panels were submerged in a copper sulfate solution (70% water, 20% copper sulfate, 10% hydrochloric acid) for 15 seconds. The panels were then removed from the solution, rinsed with deionized water, dried, and immediately rated. The copper sulfate solution etched any area of the panel where the coating has cracked and failed. The etched wedge bent panels were then examined through a microscope at 20× power to determine how far from the impinged end along the bent radii did the coating crack. Wedge Bend results are reported as the percentage of cracked area versus total length of the wedge bent panel. The lower the number, the more flexible the coating.

As shown in Table I, when compared to the 5% Resimene HM 2608, the present invention gave better MEK Double Rubs, Wedge Bend, Acetic Acid Blush, and Acetic Acid Adhesion. When compared to the 10% Resimene HM 2608, the present invention gave similar MEK Double Rubs, but gave better Wedge Bend, Acetic Acid Blush, and Acetic Acid Adhesion.

TABLE I

|  | Wt % Crosslinker | Crosslinker | MEK DR | Wedge Bend Avg | Acetic Acid Blush | Acetic Acid Adhesion |
|---|---|---|---|---|---|---|
| Latex Polymer "A" | 0 | None | 10 | 23 | 2 | P |
|  | 5 | Resimene HM 2608 | 24 | 23 | 4 | F |
|  | 10 | Resimene HM 2608 | 100 | 35 | 4 | F |
|  | 12.3 | Example C | 100 | 15 | 6 | P |

As shown in Table II, when compared to Primid XL-552, the present invention gave better MEK Double Rubs, Acetic Acid Blush, Acetic Acid Adhesion, and Acetic Acid Blister Resistance.

TABLE II

|  | Acid/ Crosslinker Molar Ratio | Crosslinker | MEK DR | Wedge Bend Avg | Acetic Acid Blush | Acetic Acid Adhesion | Acetic Acid Blister |
|---|---|---|---|---|---|---|---|
| Latex Polymer "B" | 0 | None | 18 | 17 | 2 | P | P |
|  | 1:0.95 | Primid XL-552 | 17 | 19 | 4 | F | F |
|  | 1:0.95 | Example C | 100 | 18 | 7 | P | P |

As shown in Table III, when compared to Carbodilite V-04, the polycarbodiimide of Example C gave better MEK Double Rubs, Acetic Acid Blush, and Acetic Acid Blister Resistance.

TABLE III

|  | Acid/ Carbodiimide Molar Ratio | Crosslinker | MEK DR | Wedge Bend Avg | Acetic Acid Blush | Acetic Acid Adhesion | Acetic Acid Blister |
|---|---|---|---|---|---|---|---|
| Latex Polymer "A" | 0 | None | 10 | 23 | 2 | P | P |
|  | 1:0.95 | Carbodilite V-04 | 57 | 14 | 4 | P | F |
|  | 1:0.95 | Example C | 100 | 15 | 6 | P | P |

Aspects

1. A method of applying a crosslinked coating to a package comprising:
   (a) providing a coating composition comprising:
      (i) a carboxyl-containing polymer, and
      (ii) a polycarbodiimide having the following structural units (a) or (b) including mixtures thereof:

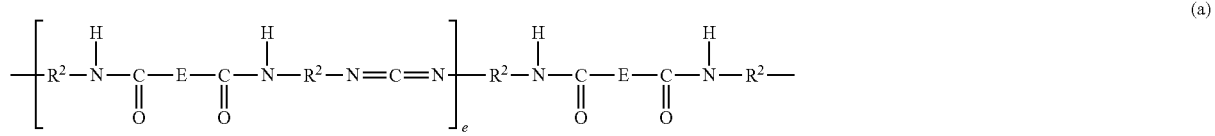

(a)

-continued (b)

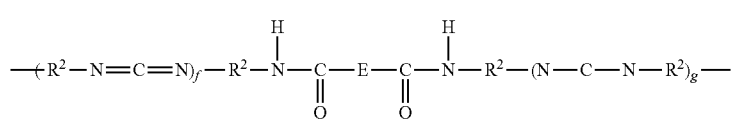

where e is an integer of from 2 to 20; f and g are each at least 1, and f+g is an integer up to 20; E is a radical selected from

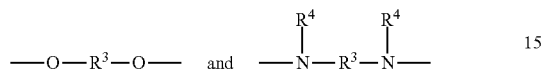

where $R^2$ comprises a cyclic radical and $R^3$ is a linear hydrocarbon radical optionally including hetero atoms containing at least 4 carbon atoms and $R^4$ is hydrogen or an alkyl radical;
(b) applying the coating composition to a substrate prior to or after forming the substrate into a package or a portion thereof; and
(c) heating the coated substrate to a temperature and for a time sufficient to crosslink the coating composition.
2. The method of aspect 1 in which the coating composition is an aqueous-based composition in which (i) and (ii) are dispersed in aqueous medium.
3. The method of any of aspect 1 or 2 in which the carboxyl-containing polymer comprises a carboxyl group-containing (meth)acrylic polymer or a carboxyl group-containing polyester polymer, including mixtures thereof.
4. The method of any of the preceding aspects in which the calculated molar ratio of carboxyl groups to carbodiimide groups is from 0.5 to 5:1.
5. The method of any of the preceding aspects in which the polycarbodiimide has a structure (a) or (b), including mixtures thereof:

(a)

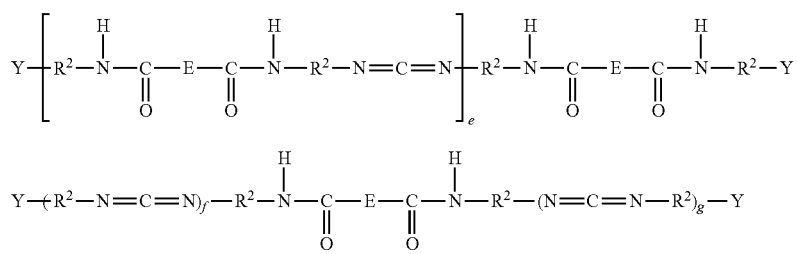

(b)

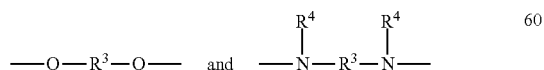

where e is an integer of from 2 to 20; f and g are each at least 1, and f+g is an integer up to 20; E is a radical selected from

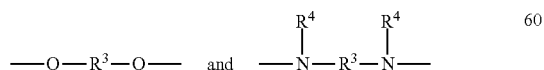

where $R^2$ comprises a cyclic radical and $R^3$ is a linear hydrocarbon radical optionally including hetero atoms containing at least 4 carbon atoms; $R^4$ is hydrogen or an alkyl radical; Y is a radical of the structure:

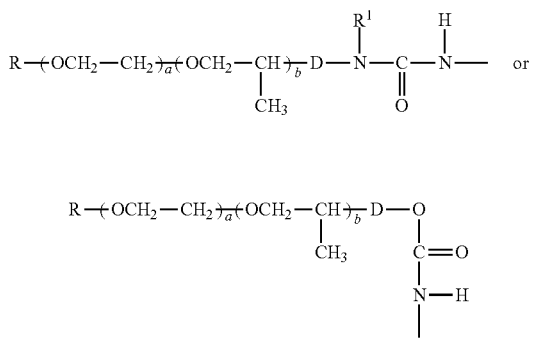

including mixed radicals, where R is $C_1$ to $C_4$ alkyl; a is 5 to 50 and b is 0 to 35, and when b is present the mole ratio of a to b is at least 1:1; $R^1$ is hydrogen or a hydrocarbon radical and D is a divalent linking group or a chemical bond.
6. The method of aspect 5 where $R^2$ comprises a cycloaliphatic radical or an alkaryl radical.
7. The method of any of aspects 5 or 6 in which the cyclic radical is of the structure:

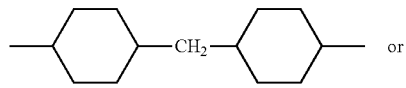 or

-continued

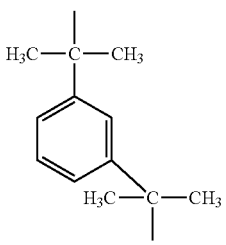

8. The method of any of aspects 5 to 7 in which E is a polyethylene moiety having a number average molecular weight of 96 to 10,000.
9. The method of any of aspects 5 to 8 in which Y comprises:

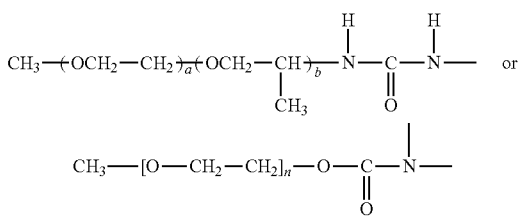

where a=15 to 25 and b=1 to 5 and the mole ratio of a:b is at least 5.
10. The method of any of the preceding aspects in which the polycarbodiimide has a weight average molecular weight of 2600 to 12,000.
11. The method of any of the preceding aspects in which the polycarbodiimide has a diimide equivalent weight of at least 600.
12. The method of any of the preceding aspects in which the package is a food or beverage container.
13. The method of aspect 12 in which the coating composition is applied to the food-contacting surface of the container or to a can end.
14. The method of any of the preceding aspects in which
   the substrate is formed into a food or beverage container and the coating composition applied to the food or beverage container; or
   the coating composition is applied to a planar substrate, preferably the coating composition is applied continuously to a length of coil metal sheet stock; the coating composition is heated for a time and temperature sufficient to crosslink the coating composition; the substrate is formed into a food or beverage container or a portion thereof.
15. A coated package comprising a coating applied to the surface of the package, the coating being derived from a composition as defined in any of aspects 1-11.
16. The coated package of aspect 15 in which the package is defined as in any of aspects 12 or 13.

Whereas particular embodiments of this invention have been described above for purposes of illustration, it will be evident to those skilled in the art that numerous variations of the details of the present invention may be made without departing from the invention as defined in the appended claims.

Although various embodiments of the invention have been described in terms of "comprising", embodiments consisting essentially of or consisting of are also within the scope of the present invention.

The invention claimed is:
1. A coated package comprising a coating applied to the surface of the package, the coating being derived from a composition comprising:
   (a) a carboxyl-containing polymer, and
   (b) a polycarbodiimide having the following structural units (a) or (b) including mixtures thereof:

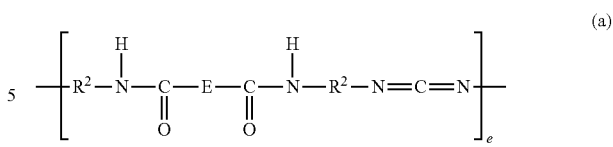

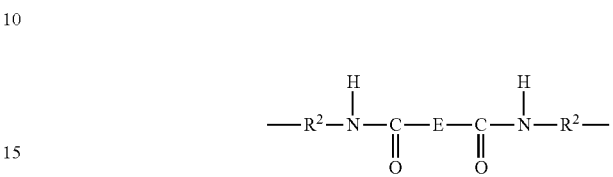

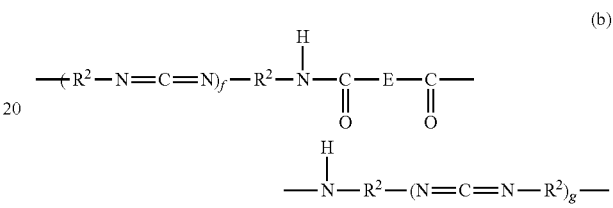

where e is an integer of from 2 to 20; f and g are each at least 1, and f+g is an integer up to 20; E is a radical selected from

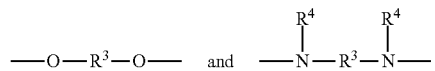

where $R^2$ comprises a cyclic radical and $R^3$ is a linear hydrocarbon radical containing at least 4 carbon atoms and $R^4$ is hydrogen or an alkyl radical.

2. The coated package of claim 1 in which the composition is an aqueous-based composition in which (a) and (b) are dispersed in aqueous medium.

3. The coated package of claim 1 in which the carboxyl-containing polymer comprises a carboxyl group-containing (meth)acrylic polymer or a carboxyl group-containing polyester polymer, including mixtures thereof.

4. The coated package of claim 1 in which the calculated molar ratio of carboxyl groups to carbodiimide groups is from 0.5 to 5:1.

5. The coated package of claim 1 in which the polycarbodiimide has a weight average molecular weight of 2600 to 12,000.

6. The coated package of claim 1 in which the polycarbodiimide has a diimide equivalent weight of at least 600.

7. The coated package of claim 1 in which the package is a food or beverage container.

8. The coated package of claim 7 in which the coating is applied to a food-contacting surface of the container.

9. The coated package of claim 7 in which the coating composition is applied to a can end.

10. The coated package of claim 1 in which the polycarbodiimide has a structure comprising (a) or (b), including mixtures thereof:

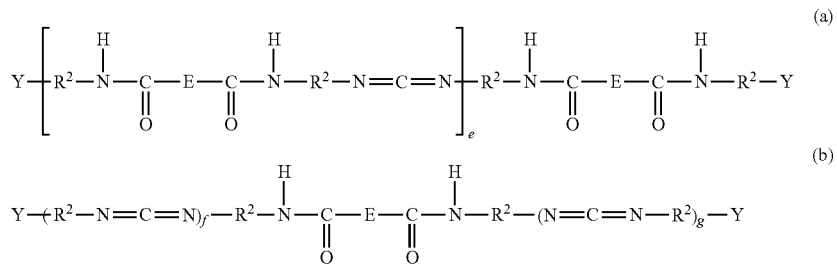
(a)

(b)

where e is an integer of from 2 to 20; f and g are each at least 1, and f+g is an integer up to 20; E is a radical selected from

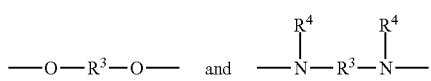

where $R^2$ comprises a cyclic radical and $R^3$ is a linear hydrocarbon radical containing at least 4 carbon atoms; $R^4$ is hydrogen or an alkyl radical; Y is a radical of the structure:

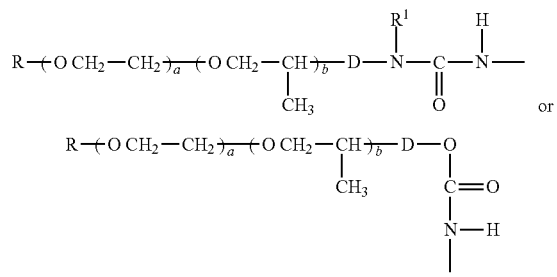

including mixed radicals, where R is $C_1$ to $C_4$ alkyl; a is 5 to 50 and b is 0 to 35, and when b is present the mole ratio of a to b is at least 1:1; $R^1$ is hydrogen or a hydrocarbon radical and D is a divalent linking group or a chemical bond.

11. The coated package of claim 10 where $R^2$ comprises a cycloaliphatic radical or an alkaryl radical.

12. The coated package of claim 11 in which the cyclic radical is of the structure:

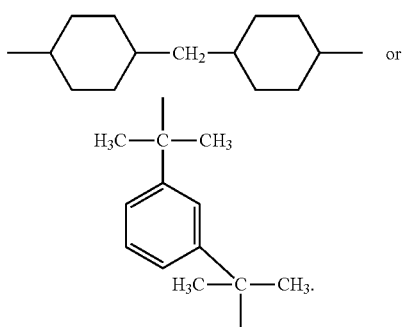

13. The coated package of claim 10 in which E is a polyethylene moiety having a number average molecular weight of 96 to 10,000.

14. The coated package of claim 10 in which Y comprises:

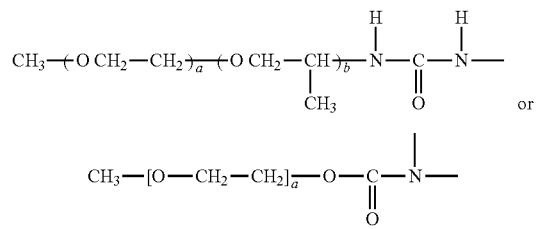

where a=15 to 25 and b=1 to 5 and the mole ratio of a:b is at least 5.

15. A method of applying a crosslinked coating to a package comprising:
(a) applying the coating composition of claim 1 to a substrate prior to or after forming the substrate into a package or a portion thereof; and
(b) heating the coated substrate to a temperature and for a time sufficient to crosslink the coating composition.

16. The method of claim 15 in which the coating composition is an aqueous-based composition in which (i) and (ii) are dispersed in aqueous medium.

17. The method of claim 15 in which the carboxyl-containing polymer comprises a carboxyl group-containing (meth)acrylic polymer or a carboxyl group-containing polyester polymer, including mixtures thereof.

18. The method of claim 15 in which the calculated molar ratio of carboxyl groups to carbodiimide groups is from 0.5 to 5:1.

19. The method of claim 15 in which the package is a food or beverage container.

20. The method of claim 19 in which the coating composition is applied to the food-contacting surface of the container.

21. The method of claim 19 in which the coating composition is applied to a can end.

22. The method of claim 15 in which the coating composition is applied to a planar substrate; the coating composition heated for a time and temperature sufficient to crosslink the coating composition; forming the substrate into a food or beverage container or a portion thereof.

23. The method of claim 22 in which the coating composition is applied continuously to a length of coil metal sheet stock.

* * * * *